US012613190B2

(12) United States Patent
Tafas et al.

(10) Patent No.: US 12,613,190 B2
(45) Date of Patent: Apr. 28, 2026

(54) QUANTITATIVE LIQUID BIOPSY DIAGNOSTIC SYSTEM AND METHODS

(71) Applicant: QCDx, LLC, Farmington, CT (US)

(72) Inventors: Triantafyllos P. Tafas, Rocky Hill, CT (US); Seth Winfree, Plainfield, IN (US)

(73) Assignee: QCDX LLC, Farmington, CT (US)

( * ) Notice: Subject to any disclaimer, the term of this patent is extended or adjusted under 35 U.S.C. 154(b) by 994 days.

(21) Appl. No.: 16/626,048

(22) PCT Filed: Jun. 27, 2018

(86) PCT No.: PCT/US2018/039660
§ 371 (c)(1),
(2) Date: Dec. 23, 2019

(87) PCT Pub. No.: WO2019/005902
PCT Pub. Date: Jan. 3, 2019

(65) Prior Publication Data
US 2021/0018441 A1      Jan. 21, 2021

Related U.S. Application Data

(60) Provisional application No. 62/525,366, filed on Jun. 27, 2017.

(51) Int. Cl.
*G01N 21/64* (2006.01)
*G01N 33/487* (2006.01)
(Continued)

(52) U.S. Cl.
CPC ....... *G01N 21/6458* (2013.01); *G01N 33/487* (2013.01); *G01N 33/50* (2013.01); *G01N 2015/1445* (2013.01); *G02B 21/16* (2013.01)

(58) Field of Classification Search
CPC ............ G02B 21/0032; G02B 21/0076; G02B 21/082; G02B 21/10; G02B 21/367;
(Continued)

(56) References Cited

U.S. PATENT DOCUMENTS

| 5,785,926 A | 7/1998 | Seubert et al. |
| 6,033,880 A | 3/2000 | Haff et al. |

(Continued)

FOREIGN PATENT DOCUMENTS

| CA | 2042808 C | * | 4/2000 |
| CA | 3004285 A1 | * | 5/2017 |

(Continued)

OTHER PUBLICATIONS

Supplementary Partial European Search Report dated Oct. 9, 2020 for Application Serial No. EP 18825107, (8 pages).
(Continued)

*Primary Examiner* — Michelle M Iacoletti
*Assistant Examiner* — Maher Yazback
(74) *Attorney, Agent, or Firm* — WILSON SONSINI GOODRICH & ROSATI

(57) ABSTRACT

The present invention provides a quantitative liquid biopsy diagnostic system and methods for performing diagnostic assays. The system offers a liquid biopsy method using circulating tumor cells (CTCs) or White Blood Cells (WBC) subpopulations for precision cancer diagnosis, early detection of disease evolution, and cancer patient management. The invention utilizes selective plane illumination microscopy (SPIM) to deliver high sensitivity and specificity for the detection and isolation of individual CTCs, superseding the efficacy of existing methodologies for early cancer detection. Isolated CTCs can be analyzed for their molecular fingerprint, which can lead to matching genetic abnormalities with specific drug treatments. The system allows ex vivo observation of live CTC or WBC response to treatment. This observation of live cells offers the oncologist a new potential for optimizing therapeutic protocols by testing a patient's own cells, and then administering treatment to the patient
(Continued)

Figure 1:
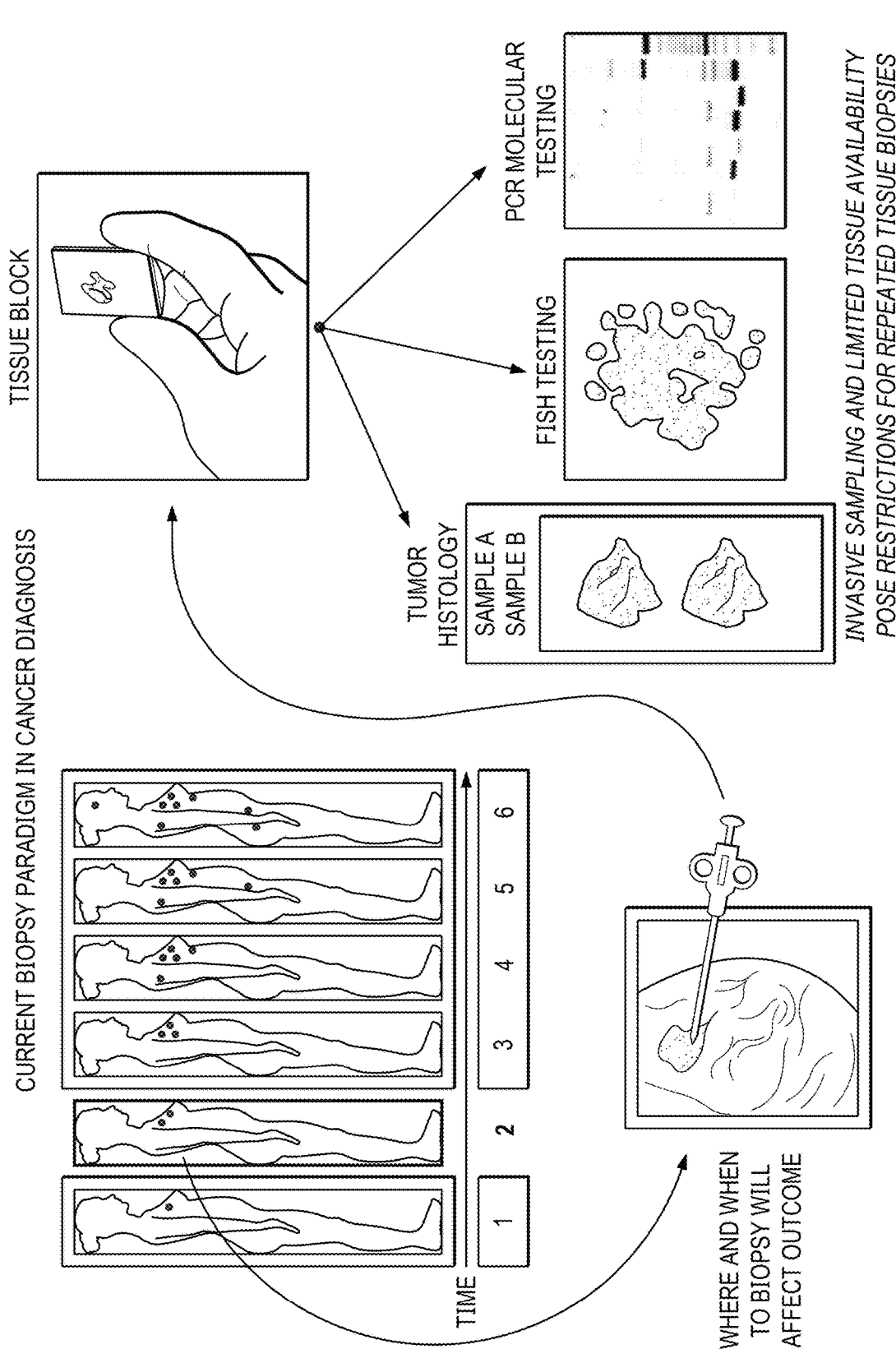

with the expectation of improving efficacy and reducing toxicity to normal cells.

13 Claims, 7 Drawing Sheets

(51) Int. Cl.

| | | |
|---|---|---|
| *G01N 33/50* | (2006.01) | |
| *G01N 15/1434* | (2024.01) | |
| *G02B 21/16* | (2006.01) | |

(58) Field of Classification Search
 CPC .... G02B 21/26; G02B 21/6458; G02B 21/16; G02B 21/18; G02B 21/0048; G02B 21/008; G02B 21/06; G02B 2207/113; G01N 21/6458; G01N 33/4833; G01N 33/487; G01N 33/50; G01N 2015/1445; G01N 1/2813; G01N 15/1434; G01N 2015/1006; G01N 15/1468; H04N 5/2256; H04N 5/23212
 USPC ................ 356/39–41; 435/366, 287.2, 7.23; 382/133, 154; 359/388, 368
 See application file for complete search history.

(56) References Cited

U.S. PATENT DOCUMENTS

| | | | | |
|---|---|---|---|---|
| 10,802,262 | B2 * | 10/2020 | Tomer .................... | G01N 1/312 |
| 2002/0148728 | A1 | 10/2002 | Kumar et al. | |
| 2005/0047640 | A1 * | 3/2005 | Eisfeld .................... | A61P 35/00 |
| | | | | 382/133 |
| 2009/0317836 | A1 | 12/2009 | Kuhn et al. | |
| 2011/0134521 | A1 * | 6/2011 | Truong ................ | G02B 21/002 |
| | | | | 359/388 |
| 2012/0237931 | A1 | 9/2012 | Katz | |
| 2014/0087362 | A1 | 3/2014 | Szalay et al. | |
| 2015/0017661 | A1 | 1/2015 | Pirie-Shepherd et al. | |
| 2016/0128311 | A1 * | 5/2016 | Wilkie ................. | A61K 31/502 |
| | | | | 435/7.1 |
| 2016/0274107 | A1 * | 9/2016 | Cognet ................ | G01N 33/566 |
| 2017/0068086 | A1 * | 3/2017 | Tomer .................... | G02B 21/26 |
| 2017/0370709 | A1 * | 12/2017 | Mace .................... | G02B 21/361 |
| 2020/0055048 | A1 * | 2/2020 | Alvarez-Puebla ........................... | |
| | | | | B01L 3/502715 |

FOREIGN PATENT DOCUMENTS

| | | | |
|---|---|---|---|
| JP | 2009-531031 A | 9/2009 | |
| WO | WO-0121310 A2 | 3/2001 | |
| WO | WO-2017075275 A1 | 5/2017 | |

OTHER PUBLICATIONS

Pitrone et al., OpenSPIM: an open-access light-sheet microscopy platform. Nat Methods. Jul. 2013;10(7):598-599.

Alix-Panabières C, Pantel K., Challenges in circulating tumour cell research, Nat Rev Cancer. Sep. 2014;14(9):623-31. doi:10.1038/nrc3820. Epub Jul. 31, 2014. PMID: 25154812.

International Search Report dated Jan. 30, 2020 for International Application Serial No. PCT/US2019/039244, (5 pages).

Mu, Zhaomei et al., Detection and Characterization of Circulating Tumor Associated Cells in Metastatic Breast Cancer, International journal of molecular sciences vol. 17,10 1665. Sep. 30, 2016,doi: 10.3390/ijms17101665.

Peeters, D J E et al., Semiautomated isolation and molecular characterisation of single or highly purified tumour cells from Cell Search enriched blood samples using dielectrophoretic cell sorting, British journal of cancer vol. 108,6 (2013): 1358-67. doi:10.1038/bjc.2013.92.

Scher, MD, Howard I., et al., Association of AR-V7 on Circulating Tumor Cells as a Treatment-Specific Biomarker With Outcomes and Survival in Castration-Resistant Prostate Cancer, JAMA Oncol. 2016;2(11):1441-1449.doi:10.1001/jamaoncol.2016.1828.

Zhang, S., Li, L., Wang, T. et al., Real-time HER2 status detected on circulating tumor cells predicts different outcomes ofanti-HER2 therapy in histologically HER2-positive metastatic breast cancer patients, BMC Cancer 16, 526 (2016). https://doi.org/10.1186/s12885-016-2578-5.

Bidard, F.C. et al. Clinical validity of circulating tumor cells in patients with metastatic breast cancer: a pooled analysis of individual patient data. Lancet Oncol. 2014, 15, pp. 406-414.

Cohen, S.J. et al. Relationship of circulating tumor cells to tumor response, progression-free survival, and overall survival in patients with metastatic colorectal cancer. J. Clin. Oncol. 2008, 26(19), pp. 3213-3221.

Debono, J.S. et al. Circulating tumor cells predict survival benefit from treatment in metastatic castration-resistant prostate cancer. Clin. Cancer Res., 2008, 14, pp. 6302-6309.

Franken, B. et al. Circulating tumor cells, disease recurrence and survival in newly diagnosed breast cancer. Clin. Cancer Res., 2012, 14, R133.

Gualda, E.J. et al. SPIM-fluid: open source light-sheet based platform for high-throughput imaging. Biomedical Optics Express. 2015, 6(11), pp. 4447-4456.

Hayes, D.F. et al., Circulating tumore cells at each follow-up time point during therapy of metastatic breast cancer patients pedict progression-free and overall survival. Clin. Cancer Res. 2006, 12(14), pp. 4218-4224.

Huisken, J. et al. Selective plane illumination microscopy techniques in developmental biology. Development, 2009, 136, pp. 1963-1975.

Joosse, S.A. et al. Biology, detection, and clinical implications of circulating tumor cells. EMBO Mol. Med., 2015, 7, p. 1-11.

OpenSPIM, Welcome to the OpenSPIM Wiki [retrieved on 2019-30-2019]. Retrieved from the Internet <URL: http://openspim.org/Welcome_to_the_OpenSPIM_Wiki>.

Pestrin, M. et al. Final results of a multicenter phase II clinical trial evaluating the activity of single-agent lapatinib in patients with HER2-negative metastatic breast cancer and HER2-positive circulating tumor cells. A proof-of-concept study. Breast Cancer Res. Treat., 2012, 134, pp. 283-289.

International Search Report, PCT/US208/03966, mailed Oct. 25, 2018.

Dittamore, Ryan et al., Phenotypic and genomic characterization of CTCs as a biomarker for prediction of Veliparib therapy benefit in mCRPC, DOI: 10.1200/JCO.2018.36.15_suppl.5012 Journal of Clinical Oncology 36, No. 15_suppl (May 20, 2018) 5012-5012, Published online Jun. 1, 2018.

Ferrarini, Alberto et al., A streamlined workflow for single-cells genome-wide copy-number profiling by low-pass sequencing of LM-PCR whole-genome amplification products, PloS one vol. 13,3e0193689. Mar. 1, 2018,doi:10.1371/journal.pone.0193689.

* cited by examiner

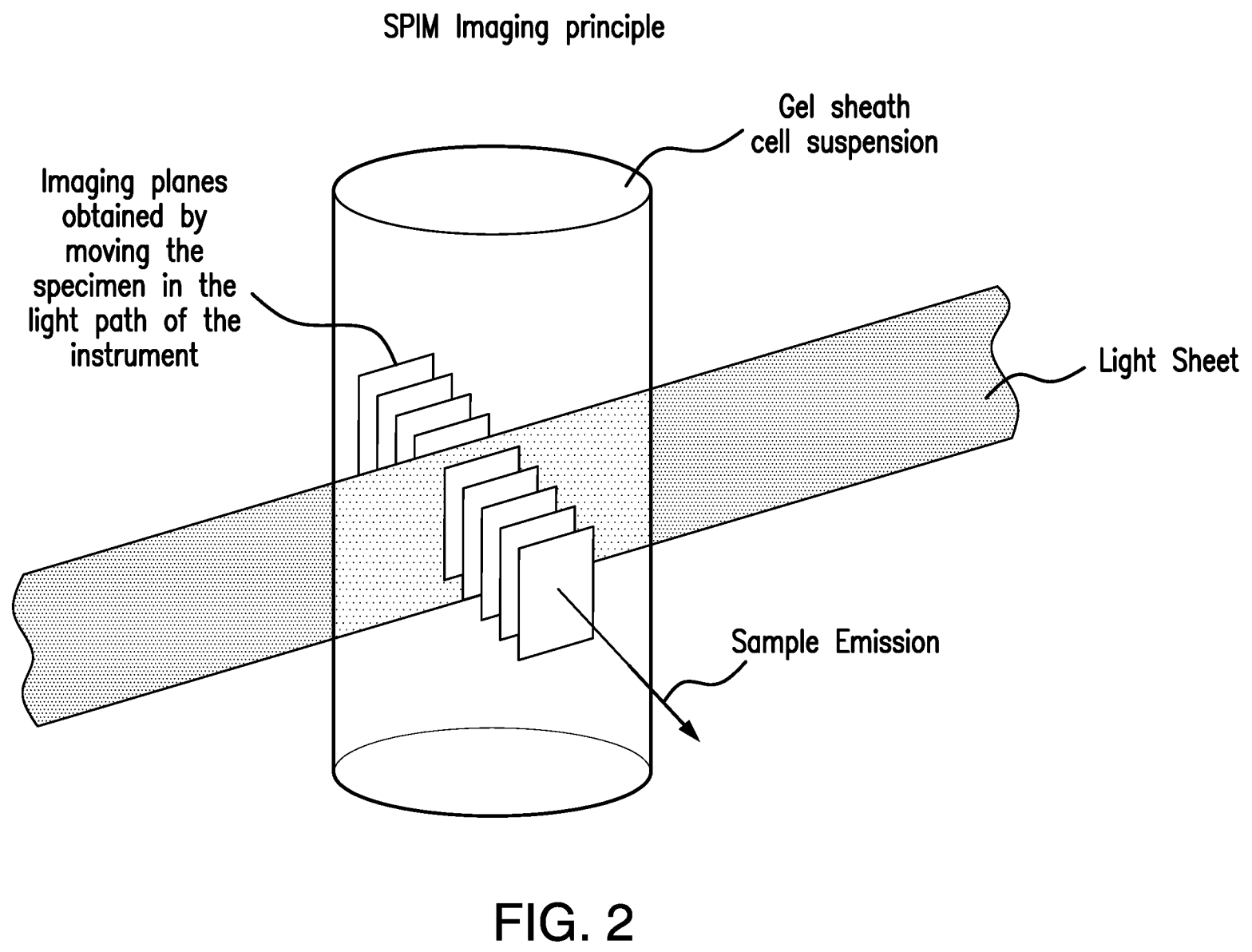

SPIM Imaging principle

Gel sheath cell suspension

Light Sheet

Sample Emission

Imaging planes obtained by moving the specimen in the light path of the instrument

FIG. 2

MONITORING EFFICACY OF CANCER THERAPY WITH SYSTEM AND METHODS OF PRESENT INVENTION

SAMPLE A
SAMPLE B

CTC TEST

INITIAL Dx
Tx SELECTION

TREATMENT
MONITOR
RESPONSE/
RESISTANCE

COMPLETE
RESPONSE

SURVEILLANCE

DISEASE
RECURRENCE
Tx SELECTION

QUANTITATIVE LIQUID BIOPSY DIAGNOSTIC SYSTEM AND METHODS

CROSS-REFERENCE

The present application is a 371 national stage entry of International Application No. PCT/US2018/039660, filed Jun. 27, 2018, which claims the benefit of U.S. Provisional Application No. 62/525,366, filed Jun. 27, 2017, each of which is incorporated herein by reference.

FIELD OF THE INVENTION

The present invention provides a quantitative liquid biopsy diagnostic system and methods for performing diagnostic assays, based on a simple blood sample. The system offers a liquid biopsy method that detects and identifies blood cell sub-populations from the patient's blood cells including rare cells such as circulating tumor cells (CTCs) for precision cancer diagnosis, early detection of disease evolution, and cancer patient management. The invention utilizes selective plane illumination microscopy (SPIM) to deliver high sensitivity and specificity for the detection and isolation of individual CTCs, superseding the efficacy of existing methodologies for early cancer detection. Isolated CTCs can be analyzed for their molecular fingerprint, which can lead to matching genetic abnormalities with specific drug treatments. The system allows ex vivo observation of live tumor cell response to treatment. This observation of live cells offers the oncologist a new potential for optimizing therapeutic protocols by testing a patient's own cells, and then administering treatment to the patient with the expectation of improving efficacy and reducing toxicity to normal cells.

BACKGROUND OF THE INVENTION

Traditional solid tissue biopsies are the gold standard for cancer diagnosis. However, these assays are static and require fixation and staining of the samples for histologic analysis by conventional microscopic techniques. This limits sample size and thickness and does not present the opportunity to more readily sample and monitor samples under dynamic conditions. For ongoing monitoring of disease progression and patient management, liquid biopsies offer a unique advantage because they involve non-invasive, blood based testing of cell-free DNA (cfDNA) or CTCs. Molecular analysis of cfDNA (including circulating tumor DNA, ctDNA) has shown high sensitivity and specificity for detecting driver mutations, structural rearrangements, copy number aberrations and changes in DNA methylation, therefore providing valuable information for disease monitoring.

However, a driver gene does not kill a patient. Rather, aggressive tumor cells do. CTC analysis permits the study of whole cells, and offers DNA, RNA and protein-based molecular profiling, as well as the opportunity for functional studies that can guide precision therapies.

CTCs have been detected in the blood of cancer patients in frequencies of $1:10^8$ to $1:10^6$ or higher. CTCs are released in the circulation from the primary tumor following a series of biological events involving epithelial to mesenchymal transition (EMT). Single tumor cells or tumor cell clusters leave the primary tumor site, invade the blood vessels, and travel throughout the body until they leave the blood stream. After a reverse, mesenchymal to epithelial transition (MET), the cells settle in different tissues, thereby generating the bud of metastasis formation. Detection of CTCs in the blood is challenging, both because of their scarcity and because they can express different phenotypes. These phenotypes include epithelial, mesenchymal and stemness-like CTCs, but with features that can change over time, converting from one state to another, and vice versa. See, Joosse et al (2015). Biology, detection, and clinical implications of circulating tumor cells. EMBO Mol Med 7: 1-11.

One of the early commercial CTC analysis systems was CellSearch® (Silicon Biosystems/Menarini) developed in the mid-2000's. This system is based on epithelial cell adhesion molecule (EpCAM) for CTC enrichment, followed by immunofluorescent staining for cytokeratin (positive CTC characterization), CD45 (which is also known as lymphocyte common antigen) to exclude leucocytes and diamidino-2-phenylindole (DAPI) for nuclear counterstaining. CellSearch validation studies showed the prognostic value of CTCs and led to FDA clearance for monitoring patients with metastatic breast, prostate and colon cancer. See, Hayes D F, et al. Circulating Tumor Cells at Each Follow-up Time Point during Therapy of Metastatic Breast Cancer Patients Predict Progression-Free and Overall Survival *Clin Cancer Res* 2006; 12 (14): 4218-4224; de Bono, J S, et al. Circulating Tumor Cells Predict Survival Benefit from Treatment in Metastatic Castration-Resistant Prostate Cancer. Clin Cancer Res 2008; 14:6302-6309; and Cohen S J, Punt C J A, Iannotti N, et al. *J Clin Oncol.* 2008; 26 (19):3213-3221.

Since the development of early commercial systems, multiple studies and trials with different endpoints have analyzed the clinical utility of CellSearch CTC enumeration. It was shown that increased CTC numbers (5 per 7.5 mL of whole blood) are associated with poor prognosis in metastatic breast cancer (MBC). A pooled study of trials conducted between 2003 and 2012 and involving 2000 MBC patients, confirmed the independent prognostic effect of CTC-count on progression-free survival (PFS) and overall survival (OS). It also confirmed that CTC-count improves the prognostication of MBC when added to full clinico-pathological predictive models, which cannot be done with serum tumor markers. See, Bidard, F C (2014). Clinical validity of circulating tumor cells in patients with metastatic breast cancer: a pooled analysis of individual patient data. Lancet Oncol. 15:406-14.

Beyond enumeration, several studies addressed the question of genotypic and phenotypic characterization of CTCs. In metastatic breast cancer (MBC), because there are several drugs that target human epidermal growth factor receptor 2 (HER2) and are beneficial in patient management, testing HER2 at the DNA, m.RNA and protein level has been extensively used. In metastatic renal cancer, dynamic changes of live versus. apoptotic CTC subpopulations were shown to be a predictive marker of response to chemotherapy. See, Pestrin et al. (2012) Final results of a multicenter phase II clinical trial evaluating the activity of single-agent lapatinib in patients with HER2-negative metastatic breast cancer and HER2-positive circulating tumor cells. A proof-of-concept study. Breast Cancer Res Treat 134: 283-289. In early breast cancer, several studies including more than 2800 patients, have shown that the detection of CTCs is independently associated with poor prognosis. See, Franken et al (2012). Circulating tumor cells, disease recurrence and survival in newly diagnosed breast cancer Breast Cancer Res, 14:R133.

Almost every CTC diagnostic system utilized today requires enrichment to increase CTC abundance from less than or equal to about $1:10^6$ in the patient blood to about 1:1000 nucleated cells which makes microscopic examination feasible. Without an enrichment step, it is very difficult to otherwise find and qualitatively or quantitatively assess the CTCs. After enrichment, the specimen is stained for CTC-specific biomarkers by immunostaining or in situ hybridization. Enrichment methods either utilize a cell surface marker (such as EpCAM) for antibody-based CTC capture or some physical separation method such as filtration. Either approach is making selective assumptions that lead to incomplete detection of all CTCs. Since CTCs are known to contribute to metastasis formation, it is important to identify and characterize them as accurately as possible.

Therefore, it is seen that the state of the art is limited either by conventional solid tissue biopsy methods or by CTC analysis systems that require a cumbersome enrichment step which can add error to the methodology. The present invention, which utilizes a new application of selective plane illumination microscopy (SPIM) provides a rapid analysis system for characterizing and quantifying CTCs under more realistic biological conditions without the need for an enrichment step, and therefore provides a useful alternative to conventional solid tissue biopsy methods.

SUMMARY OF THE INVENTION

The present invention relates to a liquid biopsy technology diagnostic system to detect and analyze CTCs and allow characterization of metastatic disease progression. It also can detect and characterize other subpopulations of blood cells such as T-cells. The highly informative diagnostic information assists the clinical oncologist to optimize patient treatment with the potential to improve patient outcomes, and reduce minimize side effects for the patient. Such a system can be operated in a licensed clinical laboratory that adheres to strict quality standards as mandated by the Centers for Medicare & Medicaid Services (CMS). It can also be provided to the clinical market as an in vitro diagnostic device (IVD) after appropriate approval by the US Food and Drug Administraion (FDA).

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIG. 1 shows a schematic diagram for a conventional, i.e. prior art, biopsy paradigm for cancer diagnosis for use in cancer treatment. In the upper left of the figure, the six silhouettes represent a representative female patient at six time points. Each dot in the silhouette represents a separate lesion site. The close-up photo of the mammogram and biopsy syringe in the lower left of the figure represents the taking of a tissue biopsy from the female patient at time point 2. This biopsy sample is then prepared as a tissue block for analysis as shown by the photo of a gloved hand holding a tissue block in the upper right of the figure. Sample aliquots are then analyzed by histology (photo of a microscope slide—left-most photo of three bottom right images), fluorescence in situ hybridization (FISH) (photo of image—middle photo of three bottom right images), and polymerase chain reaction (PCR) molecular testing (photo of PCR gels—right-most photo of three bottom right images).

FIG. 2 shows a schematic representation of the selective plane illumination microscopy (SPIM) imaging method of the present invention. A planar light sheet, such as a laser light sheet, is used to illuminate and penetrate a cell sample, such as the illustrated cylindrical gel sheath cell suspension. Multiple contiguous imaging planes can be obtained by moving the specimen in the light sheet path of the instrument. The light emission, such as the fluorescence emission, from the sample is observed perpendicular to the incident planar light sheets.

Figure 3:
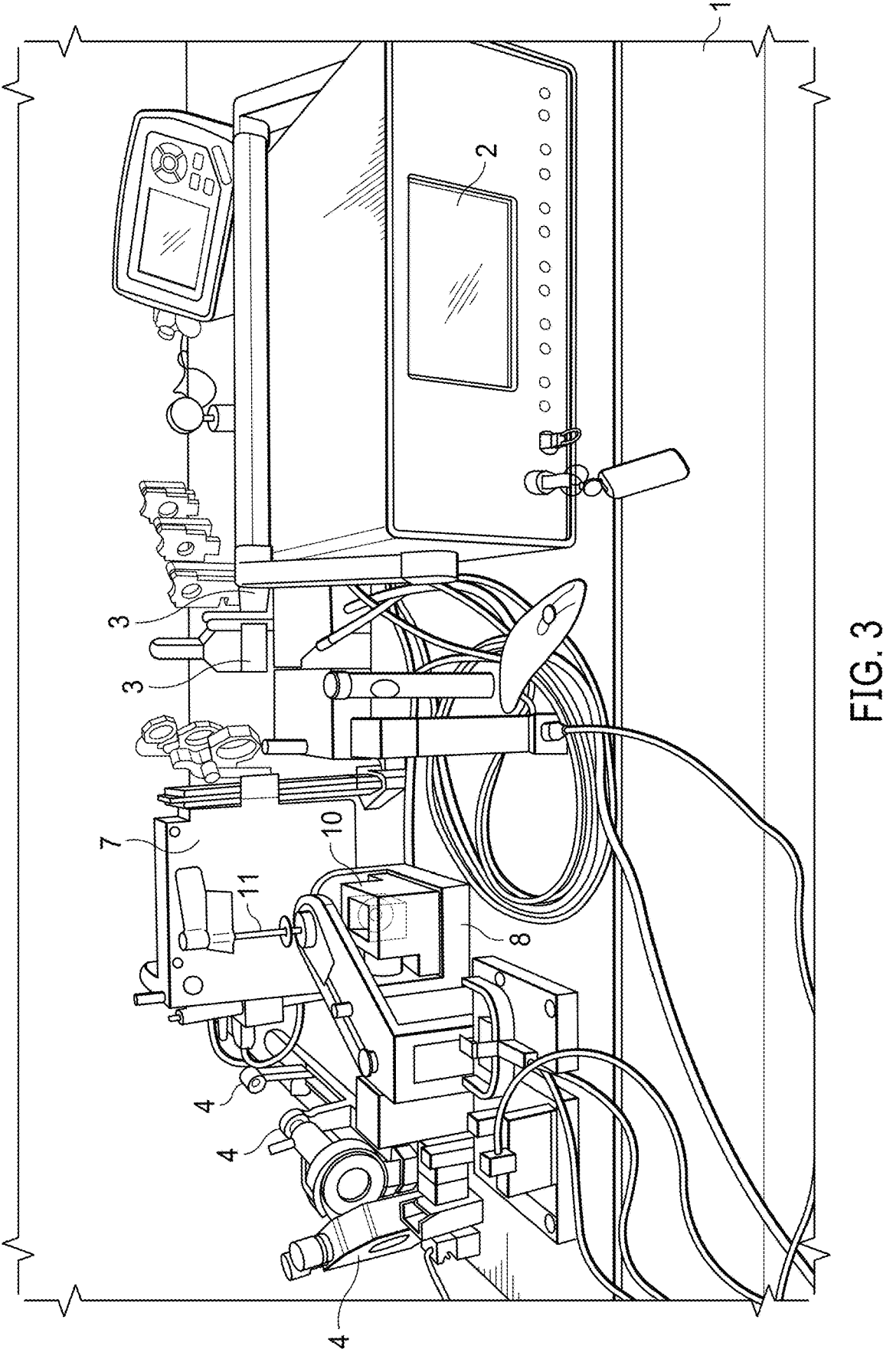

FIG. 3 shows a photograph of the instrument set up of an embodiment of the present invention. The following components are pointed out: the overall system (set-up) 1, illumination controller 2, laser light sources 3, illumination path components 4, filter wheel 7, X, Y, Z rotational stage 8, chamber (observation chamber for containing a medium such as an aqueous solution) 10, and sample (specimen) holder 11.

Figure 4:
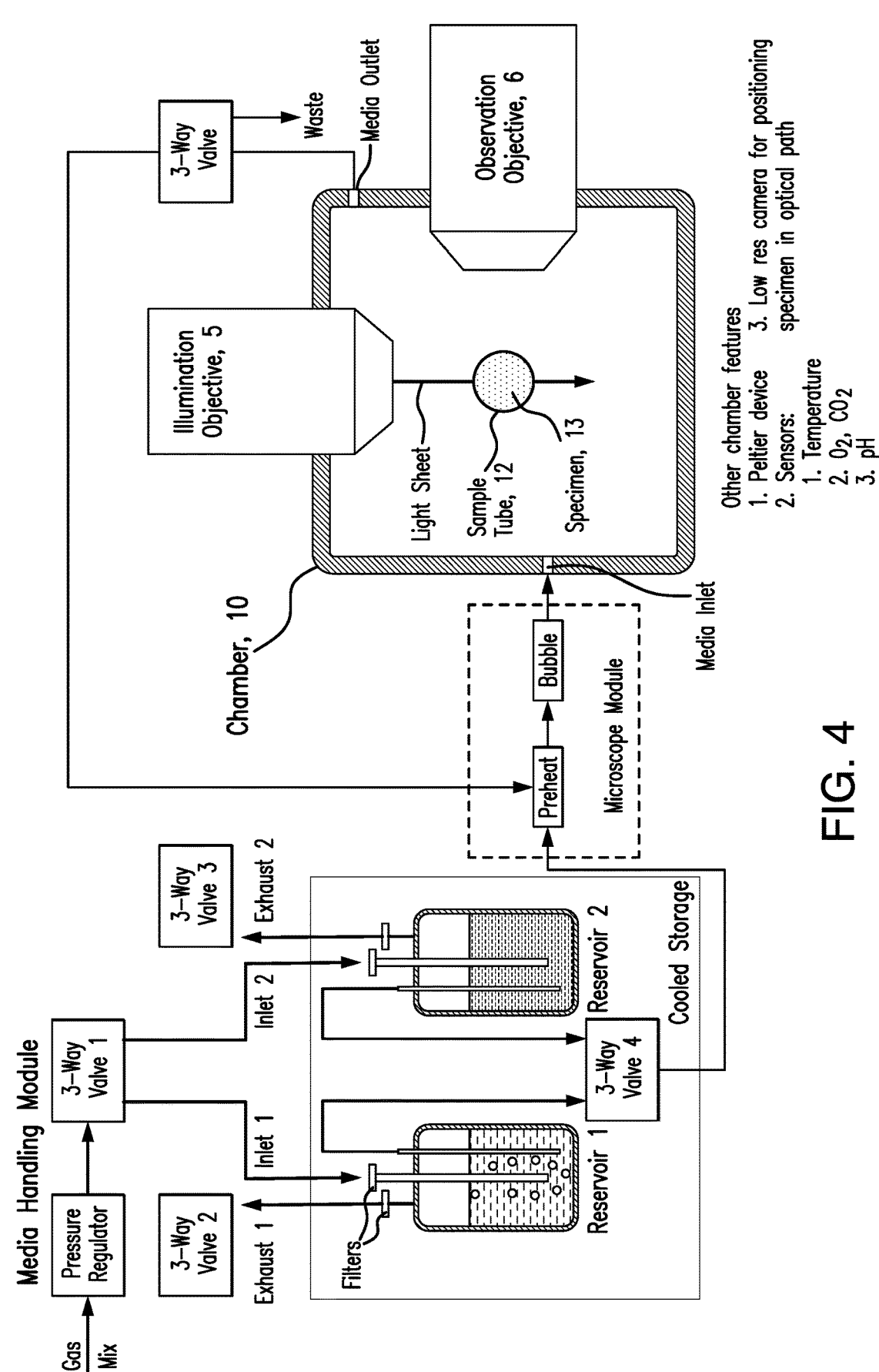

FIG. 4 shows a schematic diagram of an embodiment of the system of the present invention. Some of the illustrated components include: illumination objective lens 5, observation objective lens 6, chamber 10, sample (specimen) tube 12, sample (specimen) 13. Also illustrated are a means for providing and removing media from the chamber 10.

Figure 5:
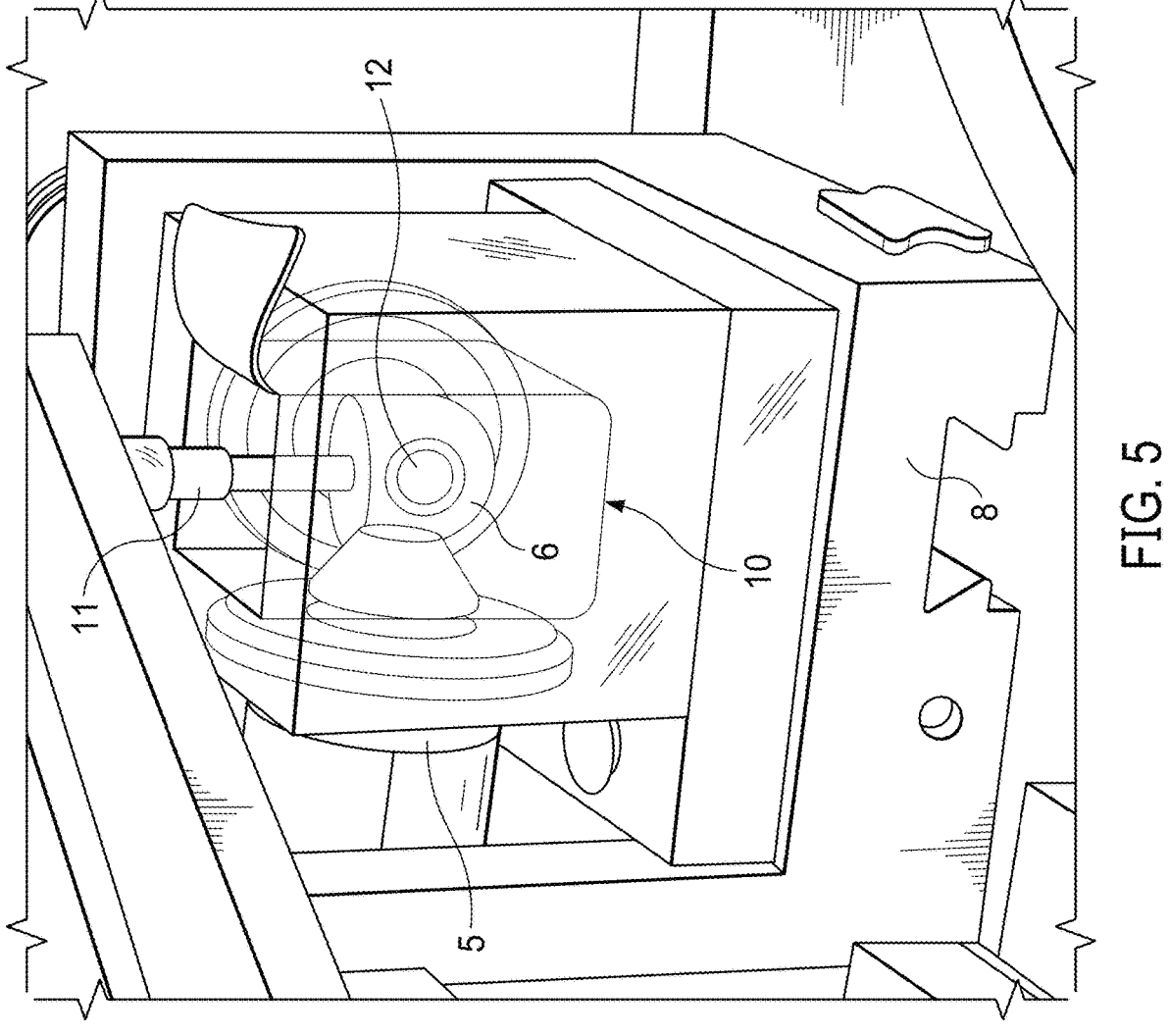

FIG. 5 shows a close-up photograph of the instrument set of FIG. 3. The following components are pointed out: illumination objective lens 5, observation objective lens 6, X, Y, Z rotational stage 8, chamber 10, sample (specimen) holder 11, sample (specimen) tube 12.

Figure 6:
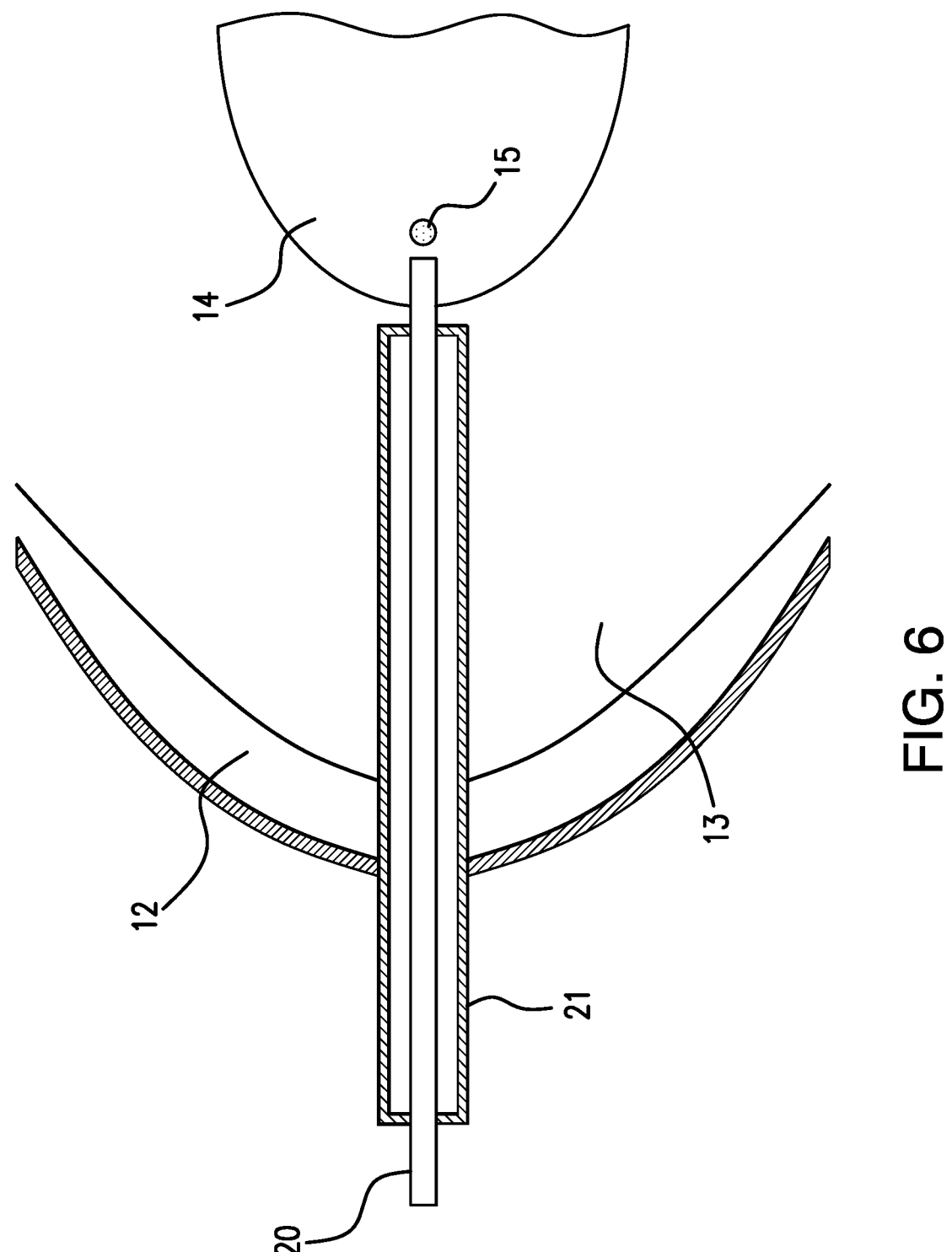

FIG. 6 is a representation of a cell-aspiration system suitable for use with the use of the present invention. Illustrated are the sample (specimen) tube 12, sample (specimen) 13, are of the sample (specimen) containing cells 14, cell of interest 15, microsyringe 20, and syringe guide 21.

Figure 7:
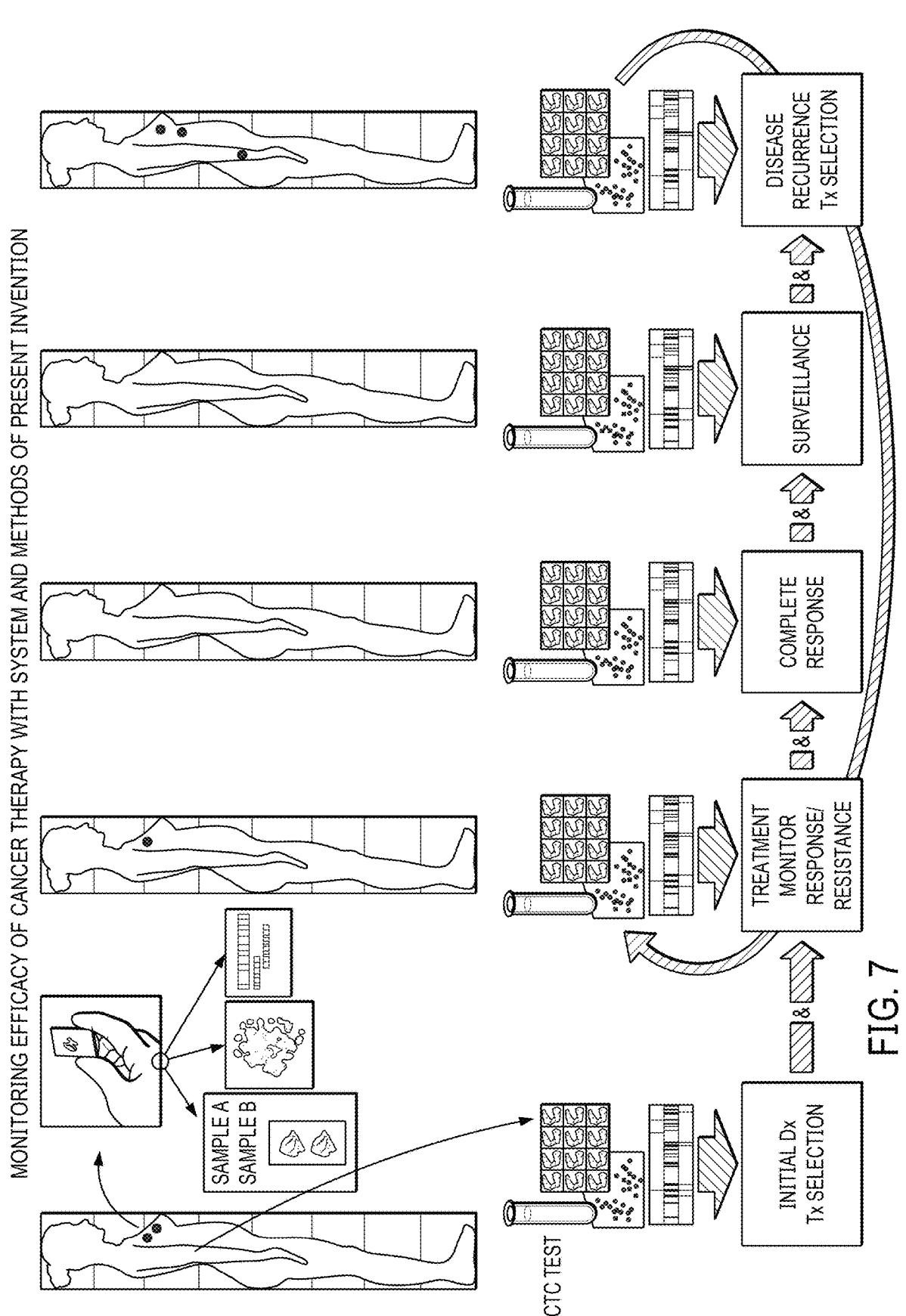

FIG. 7 shows a schematic diagram of the liquid biopsy diagnostic system and method of the present invention as it can be used in clinical practice. Across the top of the figure are five silhouettes representing a representative female patient at five time points. Each dot in the silhouette represents a separate lesion site. The close-up cluster of images emanating from the top right of the left-most silhouette represents the cluster of images form the right-half of FIG. 1, illustrating a conventional tissue biopsy and analysis. Illustrated is that the biopsy sample is prepared as a tissue block for analysis as shown by the photo of a gloved hand holding a tissue block in the upper right of the figure. The sample is then analyzed by histology (photo of a microscope slide—left-most photo of three images immediately below), fluorescence in situ hybridization (FISH) (photo of image—middle photo of three images immediately below), and polymerase chain reaction (PCR) molecular testing (photo of PCR gels—right-most photo of three images immediately below). Below each of the silhouettes is an illustration of the analysis of circulating tumor cells (CTCs) that can be quantitated and assessed from blood samples taken from the patient using the system and methods of the present invention. The system and methods can be used to monitor the efficacy of cancer therapy across time for the patient, as illustrated. The flow diagram across the bottom of the figure represents various aspects of the patient monitoring and treatment.

DETAILED DESCRIPTION OF THE INVENTION

The present invention relates to a method for characterizing and quantitating target cells in a blood sample comprising the steps of:

(a) obtaining a blood sample from a subject, (b) preparing the sample by one or more of the following steps (i) through (vi), comprising (i) centrifugation to separate cell layers from the blood serum layer (ii) removal of one of the cell layers, (iii) suspension of the removed layer from step (b)(ii) in a buffer, (iv) purification of the suspended layer of (b)(iii), (v) immobilization of the purified layer of (b)(iv), and (vi) immunostaining and/or fluorescence in situ hybridization (FISH) staining of the immobilized layer of (b)(v), (c) subjecting the prepared sample from (b) to selective plane image microscopy by scanning the sample with a light (for example a laser) sheet source at a multiple of cross sections to obtain contiguous cross-sectional images, (d) collecting a sufficient quantity of contiguous cross-sectional images, (e) compiling the contiguous cross-sectional images to produce a composite image, and (f) assessing the composite image to characterize and quantitate the blood sample for any target cells.

In another aspect the present invention relates to a method wherein the scanning of step (c) is performed at one or more selected excitation frequencies of laser sheet light.

In another aspect the present invention relates to a method wherein the collection of step (d) involves detecting the fluorescence emission of the sample orthogonal to the laser sheet light source of step (c).

In another aspect the present invention relates to a method wherein the composite image of step (f) is a 3-dimensional image.

In another aspect the present invention relates to a method wherein the layer of (b)(i) or (b)(ii) is a buffy coat layer.

In another aspect the present invention relates to a method wherein the buffer of step (b)(iii) is a phosphate buffer.

In another aspect the present invention relates to a method wherein the immobilization of step (b)(V) is in a gel that maintains cell structure such as an agarose gel, or a collagen gel, or a polyacrylamide gel.

In another aspect the present invention relates to a method wherein the subject is a mammal or bird.

In another aspect the present invention relates to a method wherein the subject is a human.

In another aspect the present invention relates to a method wherein the target cells are characterized.

In another aspect the present invention relates to a method wherein the target cells are quantitated.

In another aspect the present invention relates to a method wherein the target cells are circulating tumor cells (CTCs).

In another aspect the present invention relates to a method wherein the target cells are white blood cell (WBC) subpopulations.

In another aspect the present invention relates to a method wherein the white blood cell (WBC) subpopulation is T-cells.

In another aspect the present invention relates to a system for quantitating and characterizing target cells in a biological sample comprising:

(a) a selective plane illumination microscope (b) a sample fixture for containing the biological sample, (c) a detector for collecting the light image reflected orthogonally (90 degrees) to the illumination plane from the microscope,

(d) a computer interface, and (e) a computer to compile the light images to create a 3-dimensional image.

In another aspect the present invention relates to a system further comprising software for analyzing the 3-D mages to detect the target cells.

In another aspect the present invention relates to a system according wherein the selective plane illumination microscope comprises:

(i) a laser light source, (ii) a means for generating a light sheet from the laser light source, and (iii) an objective lens.

In another aspect the present invention relates to a system wherein the means for generating the light sheet is a cylindrical lens.

In another aspect the present invention relates to a system wherein the laser light source is a circular beam laser light source wherein the means for generating the light sheet is by scanning the laser light source in a single direction.

In another aspect the present invention relates to a method for diagnosing a disease state in a subject comprising the steps of:

(a) obtaining a biological sample from a subject, (b) subjecting the biological sample to selective plane image microscopy by scanning the sample with a laser sheet light source at a multiple of cross sections to obtain contiguous cross-sectional images, (c) collecting a sufficient quantity of contiguous cross-sectional images, (d) compiling the contiguous cross-sectional images to produce a composite image, and (e) assessing the composite image for the presence of selected target cells, and (f) making a diagnosis based on the assessment from step (e).

In another aspect the present invention relates to a method for diagnosing and treating a disease state in a subject comprising the steps of:

(a) obtaining a biological sample from a subject, (b) subjecting the biological sample to selective plane image microscopy by scanning the sample with a laser sheet light source at a multiple of cross sections to obtain contiguous cross-sectional images, (c) collecting a sufficient quantity of contiguous cross-sectional images, (d) compiling the contiguous cross-sectional images to produce a composite image, and (e) assessing the composite image for the presence of selected target cells, (f) making a diagnosis based on the assessment from step (e), and (g) treating the subject based on the diagnosis from step (f).

In another aspect the present invention relates to a method for diagnosing or diagnosing and treating a disease state wherein the subject is a human subject.

In another aspect the present invention relates to a method wherein the disease state is cancer.

In another aspect the present invention relates to a method for diagnosing or diagnosing and treating a disease state wherein the selected target cells are circulating tumor cells (CTCs).

In another aspect the present invention relates to a method for diagnosing or diagnosing and treating a disease state wherein the CTCs are characterized.

In another aspect the present invention relates to a method for diagnosing or diagnosing and treating a disease state wherein the CTCs are quantitated.

In another aspect the present invention relates to the use of selective plane illumination microscopy in the manufacture of a medicament for characterizing and quantitating selected target cells in a biological sample.

In another aspect the present invention relates to the use wherein the biological sample is a human blood sample.

In another aspect the present invention relates to the use wherein the selected target cells are circulating tumor cells (CTCs).

In another aspect the present invention relates to a method for characterizing and quantitating target cells in a blood sample which does not require enrichment or concentration of the sample obtained from step (b) for the target cells.

In another aspect the present invention relates to a method for characterizing and quantitating target cells in a blood sample wherein the sample comprises about 1 or less target cells per about $1\times10^6$ total cells (total nucleated cells) in the sample.

In another aspect the present invention relates to a method for characterizing and quantitating target cells in a blood sample wherein the sample comprises about 1 or less target cells per about $1\times10^5$ total cells (total nucleated cells) in the sample.

In another aspect the present invention relates to a method for characterizing and quantitating target cells in a blood sample wherein the sample comprises about 1 or less target cells per about $1\times10^4$ total cells (total nucleated cells) in the sample.

In another aspect the present invention relates to a method for characterizing and quantitating target cells in a blood sample wherein the sample comprises about 1 or less target cells per about $1\times10^3$ total cells (total nucleated cells) in the sample.

These and other aspects of the present invention will become apparent from the disclosure herein.

Selective Plane Illumination Microscopy (SPIM)

Light sheet fluorescence microscopy (LSFM) is a fluorescence microscopy technique in which a sample is illuminated by a laser light sheet (i.e. a laser beam which is focused in only one direction) perpendicularly (i.e. orthogonally or 90 degrees to the direction of observation. The light sheet can be created using e.g. cylindrical lens or by a circular beam scanned in one direction to create the light sheet. As has been reported, only the actually observed section of a sample is illuminated. Therefore, this method is reported to reduce the photodamage and stress induced on a living sample. Also, it has been reported that the good optical sectioning capability reduces the background signal and thus creates images with higher contrast, comparable to confocal microscopy. Furthermore, selective plane illumination microscopy (SPIM) and other fluorescence microscopy techniques in which a focused sheet of light serves to illuminate the sample have become increasingly popular in developmental studies. Fluorescence light-sheet microscopy bridges the gap in image quality between fluorescence stereomicroscopy and high-resolution imaging of fixed tissue sections. In addition, high depth penetration, low bleaching and high acquisition speeds make light-sheet microscopy ideally suited for extended time-lapse experiments. See, Huisken et al (2009). Selective plane illumination microscopy techniques in developmental biology. Development 136, 1963-1975 doi:10.1242/dev.022426. LSFM systems can be purchased from various companies such as Zeiss, Leica, or Olympus. These systems can also be built for research purposes following designs offered through open source groups such as OpenSPIM or SPIM-fluid. See, http://openspim.org/Welcome_to_the_OpenSPIM_Wiki; and https://doi.org/10.1364/BOE.6.004447.

Systems and Methods of the Present Invention

The system and method of the present invention can accurately detect epithelial, mesenchymal, or stemness-like CTCs, including intermediate phenotypes, because it is designed to quantitatively detect multiple CTC biomarkers. It provides fully automated CTC detection in patient blood samples for clinical diagnosis, academic research and drug development. The present systems does not require enrichment because its high-resolution and high-speed microscope can scan and analyze every nucleated cell from the patient sample and deliver very sensitive detection of CTCs or other blood cell subpopulations such as T-cells.

The system has the unique ability to observe live cell preparations in addition to detecting and characterizing CTCs without enrichment. The system enables (i) spatial and temporal characterization of disease progression, and (ii) observation of real time phenotypic CTC changes by ex vivo imaging.

The system of the present invention can include an aqueous solution filled cell observation chamber. This enables observation of either fixed or live cell preparation. The chamber can be equipped with a media recirculation system which enables perfusion of the cells with solutions that can contain: (i) biomarkers such as antibodies or fluorescence in situ hybridization (FISH) probes appropriately labeled for enumeration and quantitation, (ii) substances for staining DNA or other molecules, (iii) agents including therapeutic substances, viral suspensions etc. that can affect the physiology of targeted live cells, (iv) de-staining solutions, and (v) cleaning and de-contamination solutions.

The system's "lossless" CTC detection is applicable to different cancer types. By scanning every nucleated cell from the blood sample and utilizing multiple markers associated with different CTC phenotypes. The system enables detection of epithelial, mesenchymal and stemness-like CTCs. Quantitative imaging of biomarker levels also allows detection of CTCs transitioning between different CTC phenotypes.

Unlike other microscopic methods, the system's high-resolution microscopy has very low phototoxicity (i.e. the light-induced degradation of photosensitive components or in general adverse light-induced effects), which permits multiple imaging sessions of a given specimen, in successive time points.

The system of the present invention can include a cell aspiration device that allows removal of target cells from the specimen (including while live), for further molecular, single-cell testing. CTCs isolated by the system can be used as a tissue source for drug sensitivity testing by utilizing subsequent ex vivo cultures and for the detection of specific mutations in CTC-derived cell lines. In CTC-derived cell lines, cells can be studied for their resistance to specific chemotherapy or targeted therapies or combinations of the above. Drug sensitivity testing can be carried out also in mouse xenograft models. The clinical utility of the CTC models can depend on (i) the percentage of patients in which CTC will be detected and (ii) whether the CTC models can reliably capture response to different drugs. The system and methods of the present invention can aid in combining CTC genomic and transcriptomic analyses together with drug sensitivity testing in CTC-derived cell lines and mouse models; this can provide new insights for driving personalized cancer treatment.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

FIGS. 3, 4 and 5 show a quantitative liquid biopsy diagnostic system comprising a specimen chamber (reference number 10 called out in FIGS. 3 and 5), in the shape of an orthogonal parallelepiped with circular holes in all of four adjacent sides in a fashion where the two lines connecting the geometrical centers of holes on opposite sides are perpendicular to each other and parallel to the other two sides. The chamber can be made of a material with minimum coefficient of thermal expansion, allowing but negligible expansion or contraction in the temperature range of 35° to 45° C., such as a graphite composite material. Up to four objective lenses can be fitted in the four holes, in the specimen chamber, connected to an image digitization device. These lenses can be water-immersion objective lenses of appropriate magnification, numerical aperture, and working distance.

The specimen chamber 10 can contain a sensor to report temperature with an accuracy of no less than 0.001° C. A thermoelectric cooling/heating element can be installed in the specimen chamber for controlling temperature with an accuracy of no less than 0.01° C. The specimen chamber 10 can also include a liquid handling system comprising an inlet and outlet to allow changing the contents of the chamber with various liquid solutions. The liquid inlet and outlet can be operated via a digitally managed microinjection system with the injected liquid solutions being properly aerated to enable the maintenance of live cell cultures.

The system can further include a source(s) 3 of ionizing radiation positioned in the immediate vicinity of the specimen chamber 10 and is digitally operated. The system can also include a biological specimen sample holder 11 that can hold a biological specimen 13 encased in a gel sheath of a cylindrical shape. The specimen holder 11 provides a degree of rigidity so that it can sustain mechanical constraints and at the same time not interfere with live cell growth. The sample specimen holder 11 can be manufactured to not impede optical observation of the biological specimen and allow access to any portion of this specimen via a micropipette.

A microscope stage 8 manufactured for mounting a biological specimen sample holder is fitted so that it can appropriately position a biological specimen holder along the optical path of the objective lenses. The microscope stage 8 is motorized to rotate the biological specimen as well as move it in the X, Y and Z directions. A robotic arm is fitted on top of the stage so that it can load and unload a biological specimen holder in and out of the stage.

A micro-aspiration sub-system for removal of targeted portions of the biological specimen may be fitted on the side of the chamber. The micro-aspiration system allows one or more micropipettes to be guided through the walls of the chamber, e.g., into a specific position of the biological specimen. The micro-aspiration system can be fitted with an XYZ stage driving the aspiration pipette into the gel. The micro-aspiration system may be fitted with a digitally controlled microinjector (microsyringge) 20 that removes and deposits portions of the biological specimen into appropriate receptacles for further processing and analysis.

A central computer system (not shown) operates a software package that (a) acquires and processes images of the biological specimen's features for identification and quantitation, (b) actuates the motorized components, pumps, sensors of the system, (c) operates a robotic arm that loads and unloads samples, (d) actuates the ionizing radiation source, and (e) handles digital information managed in local or wide area networks. The central computer system may utilize local or distributed processing protocols.

The system also includes or is coupled to a tunable laser source or multiple single wavelength laser sources, complete with light management optical path(s). An optical system modulating the laser sheet can combine bilateral illumination to produce the sheet illumination for SPIM.

Imaging is done by illuminating the specimen with narrow spectrum excitation light provided by monochromatic and/or tunable laser sources. Images of the resulting emission are acquired by high sensitivity monochrome cameras on a field by field basis. These images are combined in 3-dimensional stacks, which are then analyzed for quantitative measurement of biomarker levels in the individual cells.

In operation, a biological specimen including live cells is stained with a variety of markers against proteins, nucleic acids or other cellular components and encased in an appropriately shaped cylindrical sheath to be fitted on a biological sample holder. The preparation is made by mixing the cell suspension with agarose or other gels compatible with preserving the subcellular structure of the embedded cells, at a temperature where the solution is still liquid. In addition to the cells, fluorescent beads that serve the role of fiducial reference for the identified cells are added to the solution. The liquid cell/bead/gel suspension is aspirated in tubing that is chosen to be transparent to the fluorescence light regime utilized. After being allowed to solidify, the specimen can be visualized in the light path. The biological specimen 13 is mounted on a specimen holder loaded onto the microscope stage and lowered into the observation chamber 10, which is filled with an aqueous solution.

The observation chamber 10 is fitted into the light path, which includes a digital camera that collects images of the specimen with a resolution appropriate for the detection and quantitation of subcellular structures revealed through the utilization of specific stains. Image analysis algorithms monitor the position of the specimen in regards to the light path and make positional corrections with direct commands to the motorized X, Y, Z, rotational specimen stage.

The specimen is imaged via water immersion optics. Imaging occurs in successive rounds so that time-lapse, 3-dimensional images of the biological sample are digitized. The biological specimen is processed via perfusion with media inserted in the chamber via the liquid handling system. Such solutions may include biologically active molecules that will react with the cells of the biological specimen. Appropriately timed and properly quantitated radiation doses may be aimed at and delivered to the biological specimen.

In operation, the system can perform some or all of the following actions:

(a) Cell suspension embedded in matrix/gel is fitted in an appropriate sample holder, then attached to the XYZ/rotational stage and inserted in the optical path.

(b) Insertion and removal of the sample holder to stage is executed by a robotic arm.

(c) The sample is analyzed automatically with the stage positioning successive areas of the specimen at an appropriate XYZ position for image acquisition.

(d) Images are acquired by successive exposure of the specimen to appropriate illumination regiments with wavelength and intensity suitable for the image acquisition of signals related to the probes used for staining the cells. Image acquisition may be done automatically by operating a high sensitivity and high-speed camera, connected to suitable speed computer system.

(e) 2-dimensional images are compiled as desired to form 3-dimensional or higher-dimensional images to reflect multiple illumination regiments and time related acquisition.

(f) Image processing can be done in real time to identify the cells and subcellular components of interest.

(g) Quantitative analysis of the signals' morphology and relative position in a given cell provides the ability to assess expression levels of specific proteins, RNA levels or DNA abnormalities.

(h) The imaging algorithmic processes can intelligently guide continuing imaging/processing of the specific specimen.

(i) Control and modifications of the specimen environment within the chamber can be handled by the computer system, provide feedback related to guide further sample analysis to achieve the goals of the predetermined analytical process.

(j) Cells of interest can be made available by isolation utilizing the micro-aspiration sub-system.

QCDS can analyze the same specimen/cell suspension multiple times. The goal may be to observe effects that different environmental factors have on the suspended cells. Such factors can include:

(a) Reagents embedded to the matrix/gel before initial cell suspension.

(b) Reagents provided to the cells in suspension via the perfused media while positioned inside the system chamber or after being removed from the chamber and prior to re-insertion.

(c) Such reagents may include substances, including therapeutic agents, used for treating the patient from which the bodily fluid (blood, cerebrospinal fluid or other) originated from. For example, in the case of cancer patients, the agents may include substances used for immunotherapy, chemotherapy etc.

(d) Radiation aimed at the cell suspension. Appropriate selection of radiation type including ionizing radiation and dosage may be used to simulate whole body patient treatment.

(e) Repeated, quantitative observation of the markers utilized for the characterization of cells of interest, such as CTC. Information collected following successive stages of in vitro treatment may prove useful for deducing efficacy of whole-body, patient treatment and potentially lead to fine-tuning treatment protocols.

(f) For the case of CTC, assessing the effect of treating cells in suspension may have additional benefits. Given the clonal nature of cancer, there is potential to observe differential response of the identified cancer cells to the subjected in vitro "treatments", applied through the methods outlined above. This may be recognized as change in the observed levels of protein expression either via antibody or RNA staining.

(g) The system's ability to (1) allow repeated observation of identified cancer cells in a cell suspension and (2) quantitatively assess CTC markers can prove a very efficient tool for modulating cancer therapeutic protocols.

Processes and Functionalities for Handling Cell Preparations

For a given type of specimen, cells can be labeled for a combination of selected biomarkers before they are suspended in the mounting gel. After being visualized in the instrument, individual cells are identified and their positions recorded with respect to a fiducial fluorescent bead constellation.

For some specimens, it may be desired to utilize a follow-up set of biomarkers after analyzing the first set and while the specimen is suspended in the cell chamber. For that purpose, the liquid handling system can feed the chamber with a series of selected media, including, for example:

(a) a de-staining solution to de-activate the first series of biomarker signals, (b) a wash solution, (c) imaging of selected target cells to verify removal of previous signals (d) a new series of labeled biomarkers, or (e) another wash cycle.

After the new set of biomarkers is applied, another imaging session is executed where either the complete specimen is re-imaged or selected cells identified on the basis of 3-dimensional map created during the first imaging cycle. The resulting 3-dimensional images are again analyzed for quantitative characterization of the applied biomarkers.

Such staining/destaining cycles may be repeated a number of times.

Depending on the type of cell preparation several considerations can be taken into account, including:

(a) For live cell analysis, the perfusion process may include utilization of cell culture media (b) Temperature, pH, conductivity, gas concentrations and other parameters may be monitored to ascertain appropriate environment for the observed cells.

(c) Physical deformation of the specimen may be monitored by imaging the fluorescent bead fiducial markers.

Cell Chamber and Media Circulation Control

FIGS. 3, 4, and 5, (reference 10 in FIGS. 3 and 5) shows a sample chamber whose internal space is of shaped to reduce uneven fluid movement and microcurrents that can disturb specimen stability while imaged. This chamber is in fluid communication with a media storage and circulation unit that holds containers for media, cleaning solutions, and therapeutic agents, which can be infused into the media just before feeding to specimen. Gas controls enable the user to set proper media gas content ($O_2$, $CO_2$ etc.). Likewise, temperature and disinfection controls (UV-based or otherwise) enable the user heat, cool, and disinfect media in the chamber. The cell chamber circulation controls include a temperature control for meeting specimen requirements, a de-bubbler to prevent gas release in the chamber, and media re-circulation system. The chamber's environmental controls and sensors include a Peltier temperature control, gas sensors, pH/conductivity sensors, and a particulate matter load sensor.

Specimen Holder and Stage

The sample preparation and mounting procedure embeds the cell suspension in an optically transparent matrix/gel, appropriately shaped, for example into a cylinder. The mounting gel can be a low-melting point agarose, collagen gel, or other suitable material. In the case of live cell observation the chosen material permits three-dimensional cell culture.

The gel enclosed cell suspension will be mounted into the specimen sample holder which may then be automatically, positioned by the specimen stage in the light sheet path. The specimen holder provides a degree of rigidity so that it can accommodate mechanical constraints without interfering with live cell growth during time-lapse acquisitions.

The specimen sample holder is compatible with a micro-aspiration sub-system that can physically remove targeted cells from the enclosure.

The specimen stage 8 provides rotational as well as X, Y, Z movement of the cylindrical cell enclosure to allow multi-view imaging.

Cell Micro-Aspiration System

The present invention can be used in conjunction with a conventional cell aspiration system. FIG. 6 shows a micro-aspiration system that can be used to manipulate cells in a specimen in the sample chamber. Cells of interest 15 can be removed from the specimen by inserting a micropipette (microsyringe) 20 driven into the gel through a microman-ipulator. A micromanipulator is handled by a motorized stage including the micro-aspiration sub-system for removal of targeted cells 15. The micromanipulator system allows one or more micropipettes 20 to be guided through the walls of the chamber 10 and into a specific area of the biological specimen/sample 13 containing the cells 14. The computer and imaging system drives the micromanipulator via 3-di-mensional mapping-based guidance. The micropipette may be filamented, which facilitates filling the chamber with media and allows the micropipette to serve as a light conduit for illuminating the specific cell in a targeted manner. In addition to allowing micro-aspiration of targeted cells, the system can also use sub-micron micropipettes which can facilitate microinjection of substances into target cells.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exem-plary and that the actual parameters, dimensions, materials, and/or configurations will depend upon the specific appli-cation or applications for which the inventive teachings is/are used. Those skilled in the art will recognize or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be prac-ticed otherwise than as specifically described and claimed. Inventive embodiments of the present disclosure are directed to each individual feature, system, article, material, kit, and/or method described herein. In addition, any combina-tion of two or more such features, systems, articles, mate-rials, kits, and/or methods, if such features, systems, articles, materials, kits, and/or methods are not mutually inconsis-tent, is included within the inventive scope of the present disclosure.

Also, various inventive concepts may be embodied as one or more methods, of which an example has been provided. The acts performed as part of the method may be ordered in any suitable way. Accordingly, embodiments may be con-structed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively pres-ent in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in con-junction with open-ended language such as "comprising" can refer, in one embodiment, to A only (optionally includ-ing elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be inter-preted as indicating exclusive alternatives (i.e. "one or the other but not both") when preceded by terms of exclusivity' such as "either" "one of" "only one of" or "exactly one. of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifi-cally identified within the list of elements to which the phrase "at least one" refers, whether related or unrelated to those elements specifically identified. Thus, as a non-limit-ing example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Equivalents

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

Incorporation by Reference

The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

EXAMPLES

The following examples further describe and demonstrate embodiments within the scope of the present invention. The Examples are given solely for purpose of illustration and are not to be construed as limitations of the present invention, as many variations thereof are possible without departing from the spirit and scope of the invention.

Detection of Cancer Cells in Suspension Utilizing Both Epifluorescence and SPIM Microscopy The utility of the system and methods of the present invention has been demonstrated by the imaging of samples prepared from cultured tumor cells spiked into a background of peripheral blood mononuclear cells.

Methodology

Tumor cell lines were cultured following standard protocols. The breast cancer tumor line HTB-30 was cultivated in McCoy's SA medium supplemented with 10% FBS at 37° C., 5% $CO_2$. Blood was obtained by voluntary collection.

For immunostaining, blood samples spiked with a known number of cultured tumor cells were first treated with ammonium chloride-based cell lysis solution to remove the red blood cells. The resulting white blood cell (WBC)

component was spiked with cultured cancer cells for 2-photon epifluorescence microscopy. For SPIM analysis a pure suspension of cancer cells was used. The nucleated cell pellet was then resuspended in PBS and transferred to a microfuge tube. The cells were then pelleted at 200 g for 30 seconds and gently resuspended in blocking buffer. The desired combination of fluorescently labeled antibodies in blocking buffer was then added and the cells incubated on-ice for 30 minutes.

The cells were counterstained, washed with phosphate buffer solution (PBS), and stored at 4° C. until needed.

(i) 2-Photon Imaging of Cancer Cells

Cultured tumor cells, spiked into a preparation of nucleated blood cells, were subjected to epi-fluorescence, 2-photon microscopy after immunostaining and hybridization with a mixture of fluorescent dye labeled centromeric oligonucleotide probes. Staining for both IF and FISH was done at the same time which can lead to FISH staining of either DNA or RNA for genome or transcriptome analysis.

Cancer cells were identified in a background of WBC, based on positive anti-cytokeratin ab signals and observed chromosomal aneuploidy, both used as cancer biomarkers.

These results demonstrate that 2-photon laser illumination will allow quantitative, measurement of multiple signals from immunofluorescent markers or from fluorescence-in-situ-hybridization of DNA or RNA.

The specific advantage of 2-photon microscopy is that it reduces dramatically the background due to non-specific fluorescence.

(ii) SPIM Imaging of Cancer Cells

Antibody-labeled specimens were prepared for analysis using SPIM by embedding in 0.8% low-melting-point agarose. Labeled cells were suspended in phosphate buffered saline and mixed with an equal volume of 1.6% low-melting-point agarose in PBS. The 1.6% agarose solution was prepared and brought to 37° C. prior to mixing with the antibody stained cells. The agarose-cell suspension was drawn into 1 mm Fluorinated Ethylene Propylene (FEP) tubing of the desired length attached to a 1 ml syringe and allowed to fully solidify. The sample was stored at 4° C. prior to imaging. For imaging, the agarose cylinder containing the labeled cells was visualized as is or after gently extruding the agarose cylinder from the FEP tubing.

Multiple fields of the cultured tumor cells suspension were imaged in a 3-dimensional stack along a depth of preparation exceeding 130 μm. Images were acquired using a water-immersion, 10× lens at a 1 μm step.

Image acquisition was performed using single laser lines for each individual signal. The individual image stacks were merged for visualization and image analysis.

A stack of images extending across 133 planes were collected with a z path of 1 μm. This specimen volume contains just 30 single cells while the cancer cell cluster in the middle of the field includes 22 cells. The diameter or each cell is about 25 μm and the volume of the specimen imaged is 133×463×463 μm or about $28.5 \times 10^6$ μm$^3$. An estimated number of up to about 1,500 cells can fit in that volume with appropriate packing to facilitate successful image analysis.

In the experiments for SPIM detection of cancer cells the agarose cylinder dimensions were 2.35 mm by 12 mm for a total volume of $52 \times 10^9$ μm$^3$.

17 18

It is estimated that 10 million or more nucleated cells can fit in an appropriately optimized gel preparation in a density that is appropriate for imaging.

This can lead to a 15 ml total amount of blood processed in one scanning session by the system of the present invention.

Instrument Design of the System

Selective Plane Illumination Microscopy is offered by commercial microscopy manufacturers such as ZEISS and Leica and also has been the object of academic based designs that are popular with several labs around the world. The system of the present invention was designed as an improvement over commercial systems. The operational characteristics of the system of the present invention were also tested utilizing a custom made SPIM instrument based on the openSPIM concept. See, http://openspim.org/Welcome_to_the_OpenSPIM_Wiki. A significant design element of the present invention is the need to visualize the cells immobilized in gel in which they can be kept fixed or alive for ex vivo observation. The advantage of immobilizing the cells in a gel is that individual, cells-of-interest can be visualized repeatedly, while they are perfused with different media.

The core hardware components are market available off the shelf and can be obtained from various suppliers. Below is a list of components for assembling a system of the present invention.

List of Components

Illumination components, include solid state lasers, laser path modulation optics including mirrors, slit modulator, focusing lenses, and illumination lens.

Detection optical components including observation lens, fluorescence emission filters, light path and camera optical path components. Specimen handling stage which offers X, Y, Z and rotational movement of the cell preparation.

Digital CCD or CMOS camera.

Another open-source concept is SPIM-fluid. which allows visualization of cells in liquid suspension while the liquid is pumped through a tubing. See, https://doi.org/10.1364/BOE.6.004447. This approach does not allow for target cells to be visualized in longitudinal sessions or repeatedly.

The Experimental Process for Scanning a Cancer Circulating Tumor Cell Preparation Step 1: Immobilize cells in gel such as agarose within FPE tube and mount on syringe as shown in FIG. 3.

Step 2: Perfuse agarose preparation with a solution containing fluorescently labeled antibodies against CTC-specific biomarkers such as anti-EpCAM antibody targeting an epithelial cell membrane receptor.

Step 3: Incubate for 1 hour at 4° C. followed by wash steps.

Step 4. Perfuse agarose preparation with a nuclear counterstain for live cells.

Step 5. Incubate for 10 min followed by wash steps.

Step 6: Extrude the agarose cylinder from the FPE tubing before inserting the syringe on the stage holder Step 7: After loading the syringe on the stage align the specimen in the optical path utilizing the chamber camera.

Step 8: For the specimen collect image stacks for all fluorescent channels.

What is claimed is:

1. A method for characterizing or quantitating target cells in a blood sample, the method comprising:
   (a) obtaining the blood sample from a subject,
   (b) preparing the blood sample by performing (i) through (vi), to generate a prepared sample:
      (i) centrifugation to separate cell layers from a blood serum layer of the blood sample,
      (ii) removal of a layer of the cell layers,
      (iii) suspension of the removed layer from (b)(ii) in a buffer,
      (iv) purification of the suspended layer of (b)(iii),
      (v) immobilization of the purified layer of (b)(iv), and
      (vi) immunostaining or fluorescence in situ hybridization (FISH) staining of the immobilized layer of (b)(v),
   (c) subjecting the prepared sample to selective plane image microscopy by scanning the prepared sample with a laser sheet light source at a plurality of cross-sections to obtain contiguous cross-sectional images,
   (d) collecting a sufficient quantity of the contiguous cross-sectional images,
   (e) compiling the contiguous cross-sectional images to produce a composite image, and
   (f) assessing the composite image to characterize or quantitate the blood sample for the target cells.

2. The method of claim 1, wherein the scanning of (c) is performed at one or more selected excitation frequencies of laser sheet light.

3. The method of claim 1, wherein the collecting of (d) comprises detecting a fluorescence emission of the prepared sample orthogonal to the laser sheet light source.

4. The method of claim 1, wherein the composite image of (f) is a 3-dimensional image.

5. The method of claim 1, wherein the layer of (b)(ii) is a buffy coat layer.

6. The method of claim 1, wherein the immobilization of (b)(v) is in a gel that maintains cell structure.

7. The method of claim 1, wherein the subject is a human.

8. The method of claim 1, wherein the target cells are circulating tumor cells (CTCs).

9. The method of claim 1, wherein the target cells are white blood cell (WBC) subpopulations.

10. The method of claim 1, wherein the preparing in (a) does not comprise further enrichment of the prepared sample for the target cells.

11. The method of claim 1, wherein the prepared sample comprises about 1 or less target cell per about $1 \times 10^6$ total cells in the prepared sample.

12. The method of claim 1, wherein the target cells are T cells.

13. The method of claim 1, wherein the preparing in (a) further comprises embedding a cell suspension in a mounting material, wherein the cell suspension comprises the target cells.

* * * * *